(12) United States Patent
Chattopadhyay et al.

(10) Patent No.: US 7,279,181 B2
(45) Date of Patent: Oct. 9, 2007

(54) METHOD FOR PREPARATION OF PARTICLES FROM SOLUTION-IN-SUPERCRITICAL FLUID OR COMPRESSED GAS EMULSIONS

(75) Inventors: Pratibhash Chattopadhyay, North Royalton, OH (US); Boris Y. Shekunov, Aurora, OH (US); Jeffrey S. Seitzinger, Broadview Heights, OH (US)

(73) Assignee: Ferro Corporation, Cleveland, OH (US)

( * ) Notice: Subject to any disclaimer, the term of this patent is extended or adjusted under 35 U.S.C. 154(b) by 0 days.

(21) Appl. No.: 10/534,665

(22) PCT Filed: Jun. 2, 2004

(86) PCT No.: PCT/US2004/017451

§ 371 (c)(1),
(2), (4) Date: Nov. 21, 2005

(87) PCT Pub. No.: WO2004/110603

PCT Pub. Date: Dec. 23, 2004

(65) Prior Publication Data

US 2006/0153921 A1   Jul. 13, 2006

Related U.S. Application Data

(60) Provisional application No. 60/475,269, filed on Jun. 3, 2003.

(51) Int. Cl.
*A61K 9/14*     (2006.01)
*B29B 9/00*    (2006.01)

(52) U.S. Cl. .......................................... 424/489; 264/5
(58) Field of Classification Search ................ 424/489, 424/204.1, 725; 264/5
See application file for complete search history.

(56) References Cited

U.S. PATENT DOCUMENTS

| | | | |
|---|---|---|---|
| 4,851,211 A * | 7/1989 | Adjei et al. .................... | 424/40 |
| 4,897,256 A * | 1/1990 | Adjei et al. .................... | 424/43 |
| 5,043,280 A * | 8/1991 | Fischer et al. ........... | 435/235.1 |
| 5,770,559 A | 6/1998 | Manning et al. | |
| 5,981,719 A * | 11/1999 | Woiszwillo et al. ........ | 530/410 |
| 6,095,134 A * | 8/2000 | Sievers et al. ......... | 128/200.14 |
| 6,268,053 B1 * | 7/2001 | Woiszwillo et al. ........ | 428/402 |
| 6,322,805 B1 * | 11/2001 | Kim et al. .................... | 424/426 |
| 6,397,840 B1 * | 6/2002 | Chrai et al. ............ | 128/202.25 |
| 6,998,051 B2 * | 2/2006 | Chattopadhyay et al. ... | 210/634 |

* cited by examiner

*Primary Examiner*—Sharon E. Kennedy
(74) *Attorney, Agent, or Firm*—Rankin, Hill, Porter & Clark LLP

(57) ABSTRACT

The present invention provides a method of producing particles from solution-in-supercritical fluid or compressed gas emulsions. In accordance with the method of the invention, a solution that includes a solute dissolved in a solvent is contacted with supercritical fluid or compressed gas to form a solution-in-supercritical fluid or compressed gas emulsion. The emulsion is sprayed through an orifice to create spray droplets. The supercritical fluid or compressed gas and the solvent are removed from the spray droplets resulting in the formation of particles that include the solute. In one embodiment of the invention, the solvent is removed from the spray droplets by lyophilization. In another embodiment of the invention, the solvent is removed from the spray droplets by evaporation.

9 Claims, 2 Drawing Sheets

METHOD FOR PREPARATION OF PARTICLES FROM SOLUTION-IN-SUPERCRITICAL FLUID OR COMPRESSED GAS EMULSIONS

BACKGROUND OF THE INVENTION

1. Field of Invention

The present invention relates generally to a method of producing particles from solution-in-supercritical fluid or compressed gas emulsions. More particularly, the present invention relates to a method of producing particles by spraying a solution-in-supercritical fluid or compressed gas emulsion into spray droplets and removing solvent from the spray droplets to form particles.

2. Description of Related Art

Conventional methods for producing drug particles include spray drying and jet milling. The typical spray drying technique involves spraying a solution of a solute material dissolved in a solvent into droplets and then evaporating the solvent from the droplets using hot air to form particles of the solute material. The particles obtained by spray drying typically have a broad size distribution, with the average particle size of the particles being in the micron range.

The jet milling technique involves accelerating particles in a stream of air to cause a reduction in particle size due to inter-particle collisions. Jet milling tends to produce an undesirably broad distribution of particle sizes, with only a fraction being less than 1 micron in diameter. Moreover, the shearing energy required for jet milling can degrade some biologically active materials and polymers.

Nanometer sized particles (hereinafter sometimes referred to simply as nanoparticles") have also been produced from emulsions using techniques such as emulsion evaporation and solvent extraction of emulsions. One of the drawbacks associated with the emulsion evaporation process is that the process proceeds at an undesirably slow rate, which exceeds four hours in some instances. Moreover, some of the organic solvents used in the emulsion extraction process give rise to concerns about possible environmental and health affects due to residual solvent in the resulting particles.

The solvent extraction of emulsions technique requires large amounts of solvent for extraction, which leads to large waste streams, increased cost and concerns about residual solvent toxicity.

Another technique, which is sometimes referred to as dilution by water of oil-in-water (O/W) emulsions prepared using partially water soluble organic solvents, can also be used to obtain small particles. Unfortunately, this technique can result in low nanoparticle concentrations in the final dispersion. It also uses undesirably large quantities of water.

The vacuum distillation of emulsions has also been used to produce particles. Unfortunately, the associated high operating cost makes this process economically undesirable. In addition, the processing times required for achieving a low residual solvent content in the resultant particles produced by this method is still lengthy and may cause emulsion instability.

Conventional supercritical fluid based methods for nanoparticle production include the following techniques: Rapid Expansion of Supercritical Solution (RESS), Supercritical Anti-Solvent (SAS), Gas Anti-solvent (GAS) and Aerosol Solvent Extraction System (ASES).

RESS involves precipitation of particulate material by expansion of solution of the material dissolved in supercritical fluid. Therefore, application of the process is limited to materials that are substantially soluble in the supercritical fluid (typically higher than $10^{-4}$ mole fraction).

In the SAS process, which can be operated as a continuous or a batch process, a solution containing a solute of interest dissolved in a solvent is injected into a vessel containing a supercritical fluid. Extraction of the solvent from the injected solution by the supercritical fluid leads to precipitation of the solute as particles.

GAS is a batch process whereby supercritical fluid anti-solvent is injected into a solution containing the solute to be precipitated. GAS is analogous to evaporative crystallization in some circumstances. The supercritical fluid extracts the solvent out of the solution, which causes the solid to precipitate as particles.

ASES is a continuous process for precipitating particles. The solution of interest is injected via a nozzle into a supercritical fluid stream. The supercritical fluid stream is co-injected, for example, a coaxial nozzle arrangement is used so that the inner nozzle injects the solution, and the outer nozzle injects the supercritical fluid. Alternatively, a single nozzle can be used to inject both the supercritical fluid and the solvent. Such a system is described in U.S. Pat. No. 6,372,260, which is hereby incorporated by reference in its entirety.

Unfortunately, the particle formation techniques described above generally tend to exhibit poor particle size control and uniformity. In most cases, the processes produce particles that are greater than 1 micron in diameter. This fundamental limitation is caused by the particle precipitation mechanisms. The competition between nucleation and growth phenomena creates a limitation on a mean particle diameter for each of the above conventional processes. Accordingly, it is difficult to obtain nanosized and single digit micron-sized particles for most materials, and such particles generally have an undesirably broad particle size distribution.

Carbon dioxide-Assisted Nebulization with Bubble Drying (CAN-BD) is another processing technique for producing particles using a supercritical fluid. A CAN-BD process is disclosed in U.S. Pat. No. 5,639,441, which is hereby incorporated by reference in its entirety. In CAN-BD, the solubility of supercritical or compressed $CO_2$ in water or organic solvents is used to generate small droplets or bubbles, and hot air or nitrogen is used to evaporate the solvent and form solid particles. The CAN-BD method is simple, and allows for-the processing of water-soluble compounds without use of organic solvents.

CAN-BD uses a reduced processing temperature relative to conventional spray-drying processing temperatures. Unfortunately the particles produced using this technique are usually in the micron range and have a broad size distribution. The high operating temperature also makes the process unsuitable for processing of certain proteins.

In view of the limitations of prior art processing methods, it would be desirable to provide a processing technique whereby particles could be produced having a relatively small particle size in a narrow size distribution range, at a comparatively reduced processing time and at reduced cost. It would be also be desirable to develop a process that produces particles without using undesirably large amounts of solvent. Further, it would be desirable to have a technique that provides a highly controllable means of adjusting the size of the resultant particles over a wide range.

BRIEF SUMMARY OF THE INVENTION

The present invention provides a method of producing particles from solution-in-supercritical fluid or compressed gas emulsions. In accordance with the method of the invention, a solution that includes a solute dissolved in a solvent is contacted with and dispersed in supercritical fluid or compressed gas to form a solution-in-supercritical fluid or compressed gas emulsion. The supercritical fluid or compressed gas is the continuous phase of the emulsion, and the solution is the discontinuous phase of the emulsion. The emulsion is sprayed through an orifice to create spray droplets. Each spray droplet may contain several discrete drops of solution (hereinafter sometimes referred to as "emulsion micelles"). The supercritical fluid or compressed gas and the solvent are removed from the spray droplets resulting in the formation of particles that comprise the solute. The method of the invention can be used to produce particles having an average particle size that is smaller than one micron in diameter or larger than one micron.

In a first embodiment of the invention, the emulsion is sprayed through an orifice (hereinafter sometimes referred to as a "nozzle") across a pressure drop. The supercritical fluid or compressed gas continuous phase in the spray droplets rapidly decompresses upon expansion resulting in Joule-Thomson cooling. In some cases, the cooling is sufficient to freeze some of the supercritical fluid or compressed gas into a solid state (e.g., dry ice). The temperature reduction caused by rapid expansion of the supercritical fluid or compressed gas continuous phase from the spray droplets also causes the emulsion micelles in the spray droplets to solidify into frozen particles comprising solute and frozen solvent and, in some instances when supercritical or compressed carbon dioxide is used, dry ice. The frozen particles thus formed are collected and lyophilized or freeze dried to remove the solvent and dry ice, if present, by sublimation. Removal of the solvent from the frozen particles results in the formation of particles comprising the solute. It is possible to control the size of the resulting particles by adjusting the size of the emulsion micelles.

In a second embodiment of the invention, the emulsion is sprayed through an orifice as spray droplets into a zone that is maintained at a temperature preferably greater than the boiling point of the solvent. Upon expansion, the supercritical fluid or compressed gas and the solvent are rapidly removed from the droplets, with the solvent being removed by evaporation/vaporization. Removal of the solvent from the spray droplets results in precipitation of the solute as fine particles. Each emulsion micelle within the spray droplets acts as a separate micro reactor where precipitation occurs thereby minimizing agglomeration and causing precipitation of small particles with narrow size distribution. It is possible to control the size of the resulting particles by controlling the size of the emulsion micelles.

The present invention has utility in the pharmaceutical industry, particularly for the production of pure or composite micro and nanoparticles for various drug delivery applications in the form of injectables, respiratory formulations, and targeted or controlled release particles.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Figure 1:
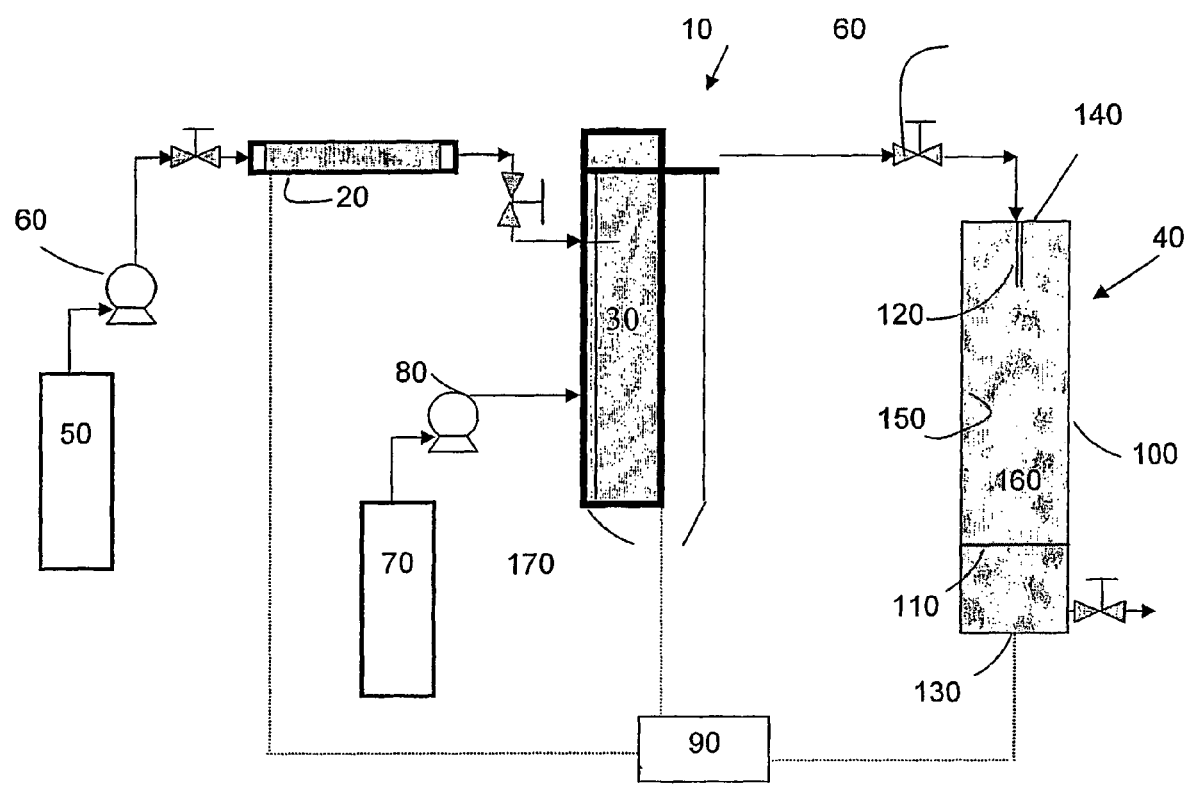
FIG. 1 is a schematic representation of an exemplary apparatus for producing particles in accordance with a first embodiment of the invention.

The present invention provides a method of producing particles from supercritical fluid or compressed gas emulsion. A solution comprising one or more solutes dissolved in a solvent is contacted with and dispersed in supercritical fluid or compressed gas to form a solution-in-supercritical fluid or compressed gas emulsion. The supercritical fluid or compressed gas is the continuous phase of the emulsion, and the solution is the discontinuous phase of the emulsion. Each discrete portion or cell of solution dispersed in the continuous supercritical fluid or compressed gas phase is sometimes referred to herein as an emulsion micelle.

In the presently most preferred embodiment of the invention, the supercritical fluid or compressed gas is carbon dioxide ($CO_2$). Carbon dioxide is supercritical when certain environmental parameters are met, namely, when the carbon dioxide is above about 304.2 Kelvin (K) and above about 7.38 megaPascal (MPa). It may also be possible to use other supercritical fluids or compressed gases such as ammonia, nitrous oxide, dimethylether, straight chain or branched C1-C6-alkanes, alkenes and combinations thereof.

The solvent used in the method of the invention should be substantially immiscible with the supercritical fluid or compressed gas. Furthermore, the solvent must have sufficient solvating power for the solute or solutes. The choice of solvent will of course be made in view of the solute or solutes to be dissolved and in view of the solubility of the solvent in the particular supercritical fluid or compressed gas. Water, which may be acidified or buffered, is the preferred solvent for use in accordance with the method of the invention.

Virtually any material that is soluble or partially soluble in the solvent(s) and sufficiently insoluble in supercritical fluid or compressed gas can be used as a solute. The present invention is particularly well suited to the production of pharmaceutical particles. Suitable pharmaceutical solute materials include, for example, medicinal agents, biologically active materials, sugars, viral materials, diagnostic aids, nutritional materials, proteins, peptides and animal and/or plant extracts. The solute material can also comprise one or more non-pharmaceutical solute materials such as, for example, agricultural chemicals, dyes, explosives, paints, polymer precursors, alkyloids, alkaloids, cosmetics, insecticides, pigments, toxins, antigens, enzymes, catalysts, nucleic acids, and combinations thereof.

It will be appreciated that the method of the invention can be utilized to produce particles comprising two or more different solute materials. If multiple solute materials are dissolved in the solvent, the resultant particles will tend to contain all of the solute constituents. If micro-encapsulates, microspheres, coated particles or co-precipitated particles are desired, a carrier or matrix material can be dissolved in the same solution with a drug or other solute material. Preferred matrix materials include polymers, fillers, disintegrants, binders, solubilizers, excipients, and combinations thereof. In particular, the matrix materials can be, for example, polysaccharides, polyesters, polyethers, polyanhydrides, polyglycolides (PLGA), polylactic acids (PLA), polycaprolactones (PCL), polyethylene glycols (PEG), ethyl cellulose and polypeptides.

One or more surfactants can be dissolved in the solution or in the supercritical fluid or compressed gas in order to facilitate the formation and/or to impart stability to the emulsion. Examples of surfactants that can be dissolved in the continuous supercritical fluid or compressed gas phase include fluorocarbons and block copolymers comprised of polymer blocks selected from the group consisting of polypropylene oxide, polyethylene oxide, poly methacrylic acid (PMMA), poly acrylic acid (PAA) and polyethylene oxide (PEO). Co-surfactants can also be dissolved in the discontinuous phase of the emulsion in order to enhance emulsion stability. Examples of co-surfactants include block copolymers comprised of polymer blocks selected from the group consisting of polypropylene oxide, polyethylene oxide, poly methacrylic acid (PMMA), poly acrylic acid (PM) and polyethylene oxide (PEO), monooleates, poly vinyl alcohol (PVA) and poly vinyl pyrolidone (PVP). The emulsions may be formed using any mixing device commonly used to disperse liquids. Examples of some emulsion forming methods include fir example: by shear using a high-pressure homogenizer, capillary nozzle or a dispersator, ultrasound, high-speed dispersator or shear mixer.

To further illustrate the formation of emulsions according to the invention, a water-soluble solute such as a biologically active compound can be dissolved in a suitable solvent such as water to form a solution. The aqueous solution comprising the biologically active compound is then dispersed in supercritical fluid or compressed gas by shear using a homogenizer, ultrasound, capillary nozzle or a dispersator. Preferably, a surfactant such as is mixed with the solution or with the supercritical fluid to assist in the formation and/or stabilization of the emulsion.

It will be appreciated that various factors such as the ratio of solution to supercritical fluid or compressed gas, the surfactant selected, and the amount of shear used to form the emulsion, can affect the size of the emulsion micelles. The use of relatively higher concentrations of surfactants and the use of greater shear mixing tends to produce smaller micelles. In addition to the concentration of the surfactant and shear mixing conditions, other factors that can be controlled to affect emulsion micelle properties include the concentration of the solute dissolved in the solvent, the concentration of solvent in the solution, temperature and pressure. The above factors are parameters that are selected to control the end-particle size and properties. Once formed, the micelles preferably remain at the desired size for extended periods of time and produce particle sizes that range preferably from 0.1 nanometers to 10 micrometers. The particle size distribution is narrowly controlled. If desired, the process parameters are controlled so that the particle sizes can range up to several microns in diameter, however particles having diameters in the nanometer range are preferred.

In a first embodiment of the-invention, the solution-in-supercritical fluid or compressed gas emulsion (hereinafter sometimes referred to simply as "the emulsion") is sprayed through an orifice such as a nozzle having one or more small openings into an expansion chamber across a pressure drop. In the spraying process the supercritical fluid or compressed gas used to form the continuous phase of the emulsion acts as a propellant and also as a coolant due to the Joule-Thomson expansion of the supercritical fluid or compressed gas from a compressed to an uncompressed state. As the emulsion expands through the orifice across the pressure drop, the cooling caused by the rapid expansion of the continuous phase of the emulsion causes the discontinuous phase to freeze as fine solid droplets. The frozen droplets, the size of which is defined by the size of the micelles in the emulsion, can be collected and accumulated in the expansion chamber. The frozen droplets are then subjected vacuum drying or lyophilization. Vacuum drying of frozen droplets removes the solvent from discontinuous phase thereby leaving the solute present in the solvent as fine particles.

In a second embodiment of the invention, the emulsion is sprayed through an orifice such as a nozzle having one or more small openings into a zone that is maintained at a temperature preferably greater than the boiling point of the solvent. The supercritical fluid or compressed gas flash into a gas, and the solvent from the micelles of the emulsion is removed by evaporation (spray drying). The temperature in the expansion chamber must be maintained at a relatively elevated temperature in order to obtain evaporation/vaporization of the solvent. Evaporation of the solvent from the drops or micelles of emulsion results in the precipitation of the solute present in the solution as dry fine particles.

The first embodiment of the invention can be carried out using an apparatus such as schematically illustrated in FIG. 1. The apparatus 10 includes an extraction column 20, a dispersion assembly 30 for forming supercritical fluid or compressed gas emulsion, an expansion assembly 40, a first supply tank 50 and a first pump 60, a second supply tank 70 and a second pump 80. A thermostat 90 communicates with the supply tanks 50, 70, the extraction column 20, the dispersion assembly 30, the expansion assembly 40 and an expansion vessel 100 to control the temperature of each unit at the desired operating conditions.

The extraction column 20 is preferably cylindrical in shape and is in fluid communication with the first supply tank 50 and the dispersion assembly 30. The thermostat 90 maintains the extraction column 20 at the desired operating temperature. The extraction column 20 can be pre-loaded with a surfactant for use in forming and/or stabilizing the emulsion. Supercritical fluid or compressed gas is supplied from the first supply tank 50 into the extraction column 20 using the first pump 60 at the desired operating pressure. The surfactant dissolves into the supercritical fluid or compressed-gas in the extraction column 20.

The dispersion assembly 30 preferably comprises either of a mixing vessel with a dispersator (shear mixer), a commercial homogenizer, an ultrasonic dispersator, a mixing vessel with impinging nozzles, or a static mixer with static mixing elements. The dispersion assembly 30 is in fluid communication with the extraction column 20 and the second supply tank 70. The surfactant laden supercritical fluid or compressed gas from the extraction column 20 is introduced into the dispersion assembly 30 using the first pump 60. Simultaneously a solution comprising a solute to be precipitated dissolved in a solvent is also introduced into the dispersion assembly 30 from the second supply tank 70 using the second pump 80. The solution and the supercritical fluid are intimately mixed in the dispersion assembly 30 to form a solution-in-supercritical fluid or compressed gas emulsion. The supercritical fluid or compressed gas comprises the continuous phase of the emulsion, and the solution comprises the discontinuous phase or micelles of the emulsion.

The expansion assembly 40, which includes an expansion vessel 100, a filter 110, and a capillary nozzle 120, is in fluid communication with the dispersion assembly 30. The expansion vessel 100 is preferably cylindrical in shape and has a first end 130 and a second end 140 that is spaced apart from the first end 130. An inner surface 150 of the expansion vessel 100 defines an expansion chamber 160.

The emulsion from the dispersion assembly 30 is expanded across a pressure drop into the expansion chamber 160 through the capillary nozzle 120. Joule Thomson cooling caused by the rapid expansion of the supercritical fluid or compressed gas causes the micelles of solution to freeze into droplets. The filter 110 is disposed inside the expansion chamber 160 to trap the frozen solution droplets inside the expansion chamber 160 during expansion.

The second pump 80 can be a high-pressure liquid chromatography (HPLC) reciprocating pump, such as the model PU-2080, which is commercially available from Jasco Inc. (Easton, Md.). The second pump 80 preferably has internal sensors that can electronically disable the second pump 80 under predetermined conditions, for example at an unsafe internal pressure. Suitable alternative second pumps include syringe type pumps, such as the 1000D or 260D pumps, which are commercially available from Isco Inc. (Lincoln, Nebr.).

The first pump 60 can be a P-200 high-pressure reciprocating pump such as is commercially available from Thar Technologies, Inc. (Pittsburgh, Pa.). Other suitable pumps include diaphragm pumps and air-actuated pumps that provide a continuous flow of fluid. The first pump 60 preferably comes factory-equipped with a burst-type rupture disc, such as is manufactured by Fike Inc. (Blue Springs, Mo.), which is plumbed into a pressure relief system. The thermostat 90 communicates with heating elements 170 that are located proximate to the dispersion assembly 30, the extraction vessel 110 and the nozzle 120.

Operation of the apparatus in accordance with the first embodiment of the invention is carried out in the following manner. First a solution comprising one or more solutes dissolved in a solvent is prepared and loaded into the second supply tank 70. The thermostat 90 is adjusted to regulate the temperature of the dispersion assembly 30 and the expansion assembly 40 at a predetermined temperature range. The second pump 80 is activated to supply a quantity of the solution to the dispersion assembly 30 at a predetermined flow rate. The first pump 60 is also simultaneously activated to supply a quantity of surfactant-saturated supercritical fluid or compressed gas from the extraction column 20 to the dispersion assembly 30 at a predetermined flow rate. The supercritical fluid or compressed gas and the solution contact each other in the dispersion assembly 30, where they intimately mix together to form a solution-in-supercritical fluid or compressed gas emulsion. As noted above, emulsions can be prepared with the aid of a rotary mixer, commercial homogenizers, ultrasonic devices, mechanical mixer or other devices known in the art for preparation of emulsions.

The emulsion is directed through the capillary nozzle 120 into the expansion chamber 160. The continuous phase of the emulsion (i.e., the supercritical fluid or compressed gas) expands upon exiting a nozzle orifice and, due to Joules-Thompson effect, decreases the temperature of the discontinuous phase below its freezing point resulting in the formation of frozen solution droplets. The size of the frozen solution droplets can be controlled by adjusting operating parameters such as, for example, nozzle geometry, pressure, temperature, flow rate, composition and concentration of the solution, choice of fluid, the presence, type and/or amount of surfactant, and combinations thereof. The gaseous expanded supercritical fluid or compressed gas is removed from the expansion chamber 160 and the filter 110 ensures that the frozen solution droplets remain in the expansion chamber 160.

If conditions are suitable within the expansion chamber 160, a portion of the supercritical fluid or compressed gas may also freeze to form, for example, particles of dry ice (solid, frozen $CO_2$). Dry ice formation is achieved when the temperature in the expansion chamber adjacent to the nozzle is below about −56.5° C. at atmospheric pressure. If dry ice formation is not desired, the thermostat 90 can be set to regulate the temperature in the expansion chamber 160 above about −56.5° C. at atmospheric pressure, and more preferably within the range of from about −56.5° C. at atmospheric pressure to about 0° C. at atmospheric pressure.

The frozen micelles of solution collected in the expansion chamber 160 are then subjected to a freeze-drying process to remove the solvent and any supercritical fluid or compressed gas. That is, the frozen droplets of solution are subjected to sublimation (phase change from solid to gas without an intervening liquid phase). Suitable freeze-drying techniques are well known in the art. As a result of the sublimation process, the particles are precipitated and are substantially devoid of solvent and supercritical fluid or compressed gas. The size and morphology of the resulting particles can be adjusted by manipulating the operating parameters previously discussed above. Particles produced by the method of the invention will generally exhibit a narrow particle size distribution.

Figure 2:
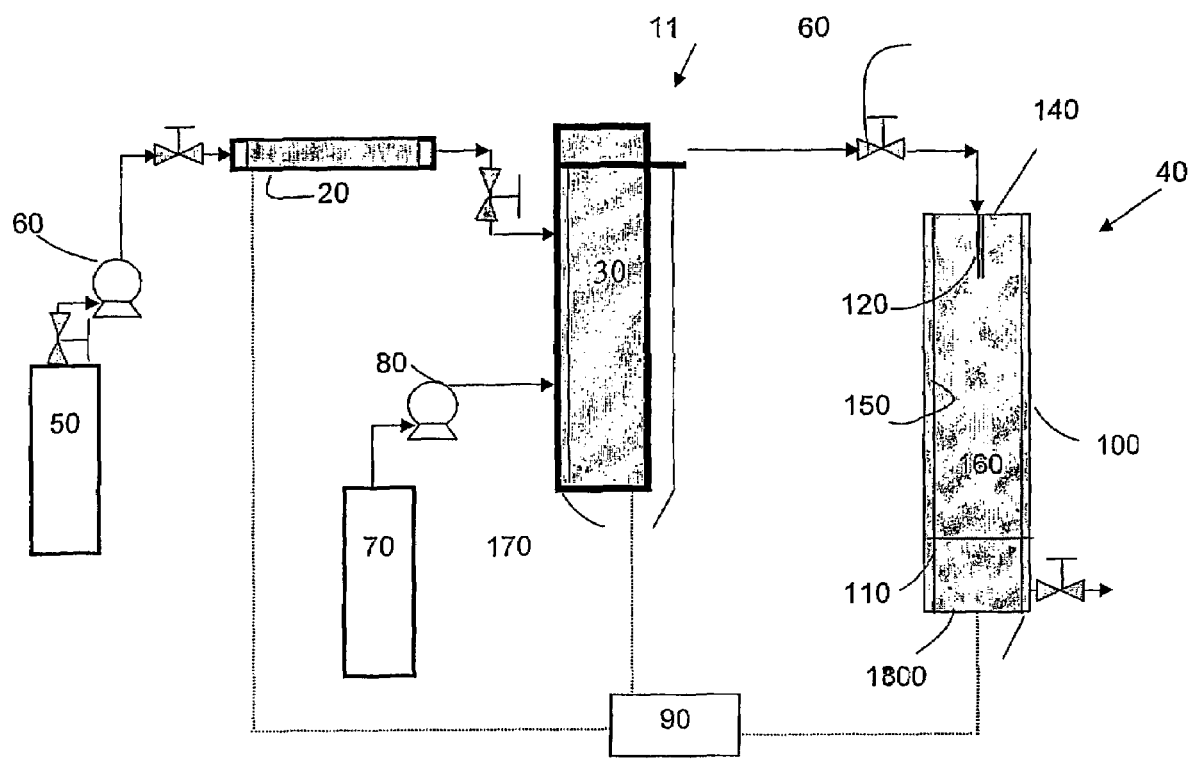
FIG. 2 is a schematic representation of an exemplary apparatus for producing particles in accordance with a second embodiment of the invention.

The second embodiment of the invention can be carried out using an apparatus 11 such as schematically illustrated in FIG. 2. Because the apparatus 11 shown in FIG. 2 is similar, in many respects, to the apparatus 10 shown in FIG. 1, the same reference numbers used in FIG. 1 are also used to identify identical components of the apparatus 11 shown in FIG. 2. The primary difference between the apparatus 11 shown in FIG. 2 and the apparatus 10 shown in FIG. 1 is that heaters 180, which are controlled by the thermostat 90, surround the expansion vessel 100 to maintain the expansion vessel 100 at a temperature above the boiling point of the solvent in the solution.

Operation of the apparatus 11 schematically illustrated in FIG. 2 is carried out in the same manner as described with respect to the apparatus 10 in FIG. 1, except for the removal of supercritical fluid or compressed gas and solvent in the expansion assembly 40. Unlike in the first embodiment of the invention, expansion of the solution-in-supercritical fluid or compressed gas emulsion occurs in the second embodiment of the invention at a temperature preferably above the boiling point of the. solvent. As the solution-in-supercritical fluid or compressed gas emulsion expands in the expansion chamber, the supercritical fluid or compress carbon dioxide flashes off as a gas and the solvent in the micelles rapidly evaporates, causing the solute to precipitate in the form of discrete, fine particles. The filter 110 ensures that the precipitated particles remain within the expansion chamber 160 as the expanded supercritical fluid or compressed gas and evaporated solvent is removed from the expansion chamber 160.

Additional advantages and modifications will readily occur to those skilled in the art. Therefore, the invention in its broader aspects is not limited to the specific details described herein. Accordingly, various modifications may be made without departing from the spirit or scope of the general inventive concept as defined by the appended claims and their equivalents.

What is claimed is:

1. A method of producing particles comprising:
providing a supercritical fluid or compressed gas having a surfactant dissolved therein;
providing a solution comprising one or more solutes dissolved in one or more solvents;
contacting the solution and the supercritical fluid or compressed gas having the surfactant dissolved therein together in a dispersion assembly to form a stabilized solution-in-supercritical fluid or compressed gas emulsion having a continuous phase comprising the supercritical fluid or compressed gas and a discontinuous phase comprising the solution;
spraying the stabilized solution-in-supercritical fluid or compressed gas emulsion through an orifice across a pressure drop in the form of spray droplets into an expansion vessel that is maintained at a pressure and a temperature sufficient to cause at least a portion of the supercritical fluid or compressed gas to decompress into a gas phase and to cause the discontinuous phase of the solution-in-supercritical fluid or compressed gas emulsion in the spray droplets to freeze and thus form frozen particles; and
freeze-drying the frozen particles to obtain particles comprising the one or more solutes that are substantially devoid of the one or more solvents and the supercritical fluid or compressed gas.

2. The method according to claim 1 wherein a co-surfactant is dissolved in the solution prior to contacting the supercritical fluid or compressed gas.

3. The method according to claim 1 wherein the solution and the supercritical fluid or compressed gas are contacted together under high shear mixing conditions to form the emulsion.

4. The method according to claim 1 wherein the particles formed after removal of the solvent have an average particle size of from about 0.1 nanometers to 10 micrometers.

5. The method according to claim 1 wherein the one or more solutes is selected from the group consisting of medicinal agents, biologically active materials, sugars, viral materials, diagnostic aids, nutritional materials, proteins, peptides, animal extracts, plant extracts and combinations thereof.

6. The method according to claim 1 wherein the one or more solutes is selected from the group consisting of agricultural chemicals, dyes, explosives, paints, polymer precursors, alkyloids, alkaloids, cosmetics, insecticides, pigments, toxins, antigens, enzymes, catalysts, nucleic acids, and combinations thereof.

7. The method according to claim 5 wherein the solution further comprises an additional solute that acts as a coating agent selected from the group consisting of polymers, fillers, disintegrants, binders, solubilizers, excipients and combinations thereof.

8. The method according to claim 7 wherein the polymer is selected from the group consisting of polysaccharides, polyesters, polyethers, polyanhydrides, polyglycolides (PLGA), polylactic acids (PLA), polycaprolactones (PCL), polyethylene glycols (PEG), polypeptides and combinations thereof.

9. A method of producing particles comprising:
providing supercritical or compressed carbon dioxide having a surfactant dissolved therein;
providing a solution comprising a biologically active material, a co-surfactant and a matrix material dissolved in water;
contacting the solution and the supercritical or compressed carbon dioxide having the surfactant dissolved therein together under high shear in a dispertion assembly to form a stabilized solution-in-supercritical carbon dioxide or compressed carbon dioxide gas emulsion having a continuous phase comprising the supercritical or compressed carbon dioxide and a discontinuous phase comprising the solution;
spraying the stabilized solution-in-supercritical carbon dioxide or compressed carbon dioxide gas emulsion through an orifice across a pressure drop in the form of spray droplets into an expansion vessel that is maintained at a pressure and a temperature sufficient to cause at least a portion of the supercritical carbon dioxide or compressed carbon dioxide gas to decompress into a gas phase and to cause the discontinuous phase of the solution-in-supercritical carbon dioxide or compressed carbon dioxide gas emulsion in the spray droplets to freeze and thus form frozen particles; and
freeze-drying the frozen particles to obtain discrete particles comprising both the biologically active material and the matrix material that are substantially devoid of carbon dioxide and water.

* * * * *